United States Patent [19]
Birnbaum et al.

[11] 3,938,506
[45] Feb. 17, 1976

[54] BLOOD PRESSURE MONITORING SYSTEM

[75] Inventors: Michael R. Birnbaum, New Brighton; Louis C. Cosentino, Wayzata, both of Minn.

[73] Assignee: Medtronic, Inc., Minneapolis, Minn.

[22] Filed: Aug. 5, 1974

[21] Appl. No.: 495,072

[52] U.S. Cl. .................. 128/2.05 A; 128/2.05 D
[51] Int. Cl.² ................................. A61B 5/02
[58] Field of Search..... 128/2.05 A, 2.05 D, 2.05 R, 128/2.05 M; 73/398 R, 402

[56] References Cited
UNITED STATES PATENTS

| | | | |
|---|---|---|---|
| 2,865,365 | 12/1958 | Newland et al. | 128/2.05 A |
| 3,533,401 | 10/1970 | Streu | 128/2.05 A |
| 3,550,582 | 12/1970 | Wilhelmson | 128/2.05 A |
| 3,714,939 | 2/1973 | Day et al. | 128/2.05 A |
| 3,814,083 | 6/1974 | Fletcher | 128/2.05 A |

OTHER PUBLICATIONS

Sandman, A.M., Med. & Biol. Engineering, May, 1974, pp. 360–363.

Med. & Biol. Engineering, 1969, Vol. 7, pp. 95–97.

*Primary Examiner*—Kyle L. Howell
*Attorney, Agent, or Firm*—Cameron, Kerkam, Sutton, Stowell & Stowell

[57] ABSTRACT

A blood pressure monitoring system is disclosed as comprising a pressure transducer coupled as by a catheter inserted into the blood vessels of a patient whose blood pressure is to be measured, for providing an output signal indicative of the patient's blood pressure, a filter for removing undesired high frequency components imposed upon the transducer output, a maximum peak detector, a minimum peak detector and a mean detector for providing outputs indicative respectively of the systolic blood pressure, the diastolic blood pressure and the mean blood pressure of the patient. Depending upon the desired indication, the output of one of the aforementioned detectors is coupled by a switch to a processing circuit for applying an output indicative of the patient's blood pressure for a selected period of time to a digital display.

5 Claims, 9 Drawing Figures

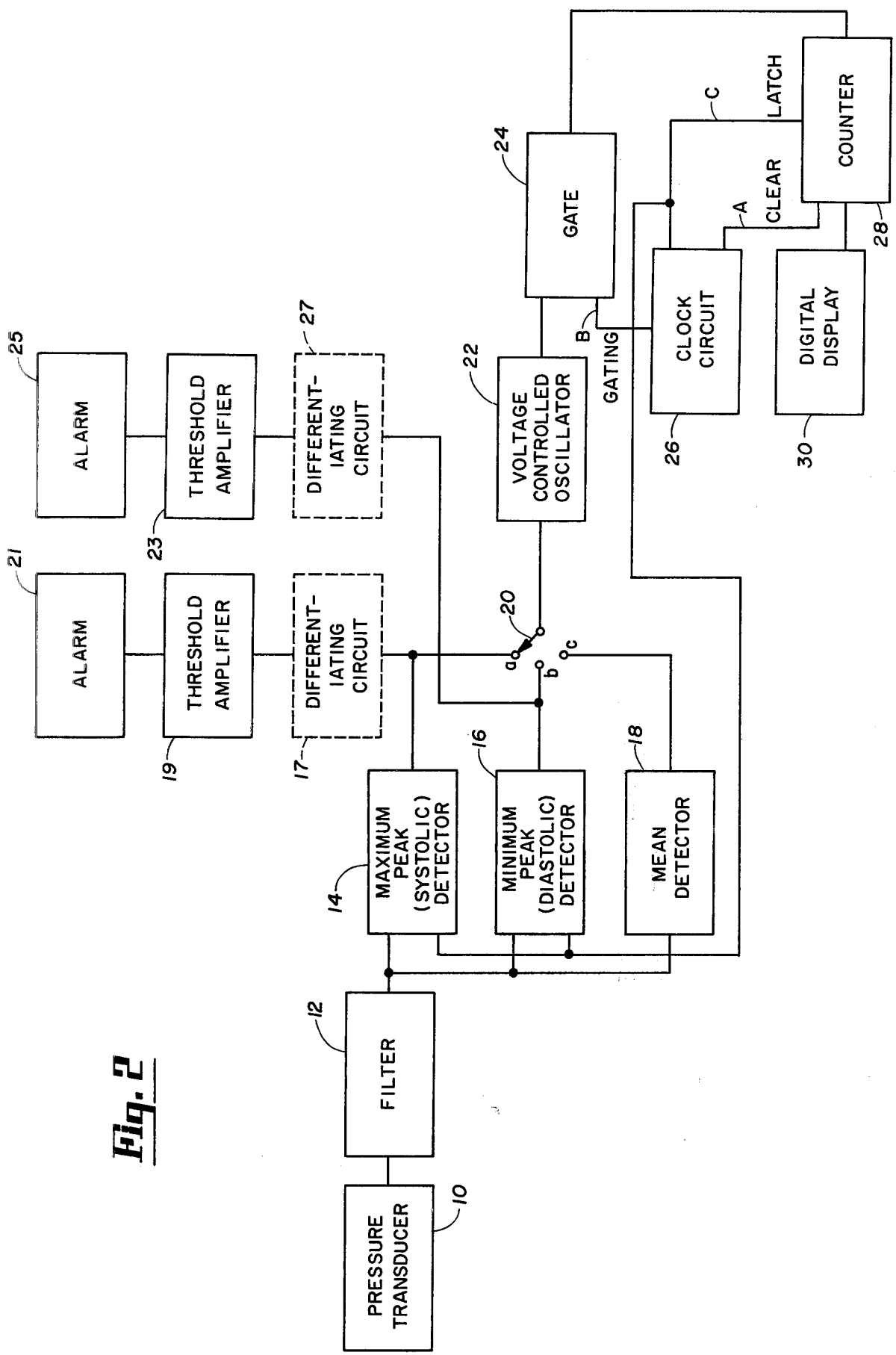

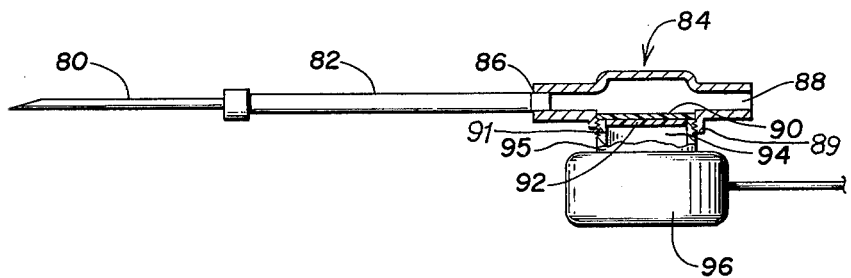
Fig. 6
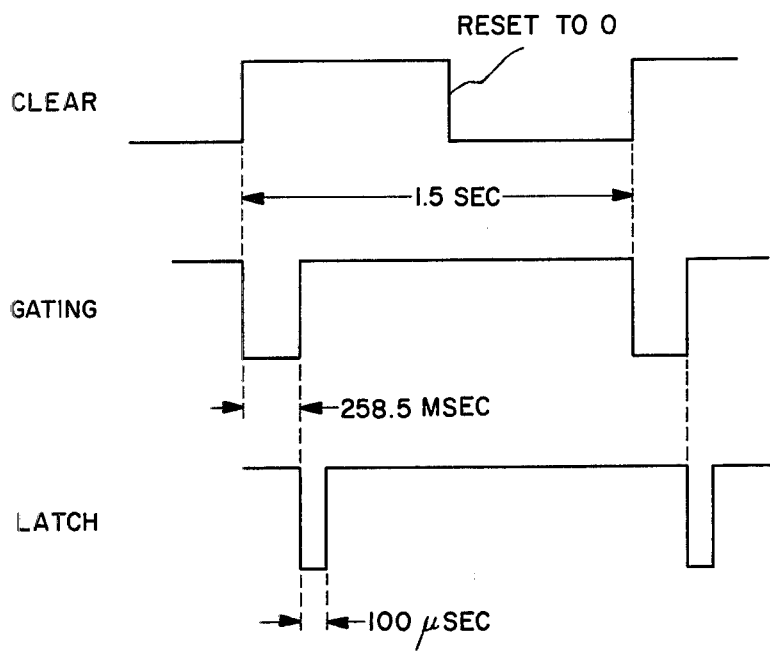
Fig. 3
Fig. 3a — CLEAR — RESET TO 0 — 1.5 SEC
Fig. 3b — GATING — 258.5 MSEC
Fig. 3c — LATCH — 100 μSEC
Fig. 4
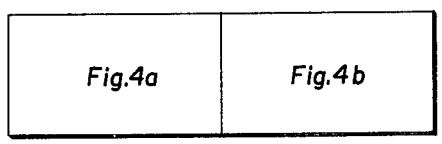
| Fig.4a | Fig.4b |

3,938,506

BLOOD PRESSURE MONITORING SYSTEM

CROSS-REFERENCE TO CO-PENDING APPLICATION

Reference is made to co-pending application Ser. No. 486,855, entitled "Blood Pressure Monitoring System", filed July 9, 1974 in the name of Michael R. Birnbaum, now U.S. Patent No. 3,893,452.

BACKGROUND OF THE INVENTION

1. Field of the Invention

This invention relates to monitoring systems and particularly those systems particularly adapted to monitor the blood pressure of a patient.

2. Description of the Prior Art

There are many applications in which it is desired to provide a portable system capable of measuring the blood pressure of a patient. For example, when a patient is coupled to an aritificial kidney, a patient may lose approximately two to three quarts of water from his vascular system. If too much water is lost, the patient's blood pressure may drop rapidly, thereby endangering the patient's life. Therefore, it is necessary to closely monitor the patient's blood pressure during such treatment so that appropriate action may be taken if his blood pressure unduly varies.

In FIG. 1, there is shown a blood pressure waveform to be measured by the blood pressure monitoring system of this invention. As the heart muscle pumps blood through the vascular system, the blood pressure varies approximately in a manner as shown in FIG. 1, having maximum points indicative of systolic blood pressure and minimum points indicative of diastolic blood pressure. Systolic blood pressure may be defined, for the purposes of this application, as the peak force per unit area with which the blood is pushing against the artery walls when the ventricles of the heart are contracting, i.e. Point A of the waveform of FIG. 1. Diastolic blood pressure is the minimum pressure exerted by the blood upon the artery walls when the ventricles are relaxed, i.e. Point B as shown in FIG. 1. The mean blood pressure "M" as labeled in FIG. 1, is defined as the average pressure of the blood pressure waveform and is defined in accordance with the following equation:

$$M = \frac{1}{T} \int p(t)dt \quad (1)$$

where $p(t)$ is the blood pressure as a function of time, and T is the period of cyclical waveform as shown in FIG. 1.

There are certain factors that affect blood pressure waveforms. Directly, arterial blood pressure is influenced by the blood volume within the arteries, which in turn is a function of the cardiac output and peripheral resistance. Therefore, any change in cardiac output or peripheral resistance may cause a change in the blood pressure waveform. Further, the cardiac output is equal to the stroke volume times the heart rate. As a result, any factor that tends to change the heart rate or stroke volume, tends to change the cardiac output. For example, an increase in cardiac output may result in a corresponding increase in blood pressure providing peripheral resistance stays constant. Peripheral resistance is defined as the fluidic resistance to blood flow. Any factor that increases the peripheral resistance, will result in an increase in the arterial blood pressure, assuming the cardiac output remains constant. The increase or decrease of the systolic, diastolic or mean blood pressure, and the amounts thereof, are indicative of designated mechanisms within the vascular system, thus indicating the status of the circulatory system.

SUMMARY OF THE INVENTION

It is therefore an object of this invention to provide a new and improved system for monitoring blood pressure and in particular the systolic, diastolic and mean blood pressures.

It is a more particular object of this invention to provide a portable blood pressure monitoring system that is capable of being manufactured at relatively low cost.

In accordance with these and other objects, there is provided blood pressure monitoring system comprising a pressure transducer coupled to the patient's body so as to measure his blood pressure, a filter for attenuating substantially any undesired, high-frequency components, and a maximum peak detector, a minimum peak detector and mean detector for respectively determining the systolic blood pressure, the diastolic blood pressure and mean blood pressure of the patient. A switch selectively couples the output of one of the aforementioned detectors to a processing circuit for applying a signal for a selected period to a display means.

BRIEF DESCRIPTION OF THE DRAWINGS

Reference is made to the accompanying drawings for a more complete understanding of the subject invention and the manner in which the above-enumerated objects are accomplished:

FIG. 2 is a schematic diagram of a blood pressure monitoring system in accordance with the teachings of this invention;

FIGS. 3A, 3B and 3C show the waveforms of selected signals as developed within the blood pressure monitoring system as shown in FIG. 2;

FIG. 6 is a sectioned, side view of a blood pressure transducer and associated catheter, capable of being incorporated into the blood pressure monitoring systems as shown in FIGS. 2 and 4.

BRIEF DESCRIPTION OF THE PREFERRED EMBODIMENTS

Figure 1:
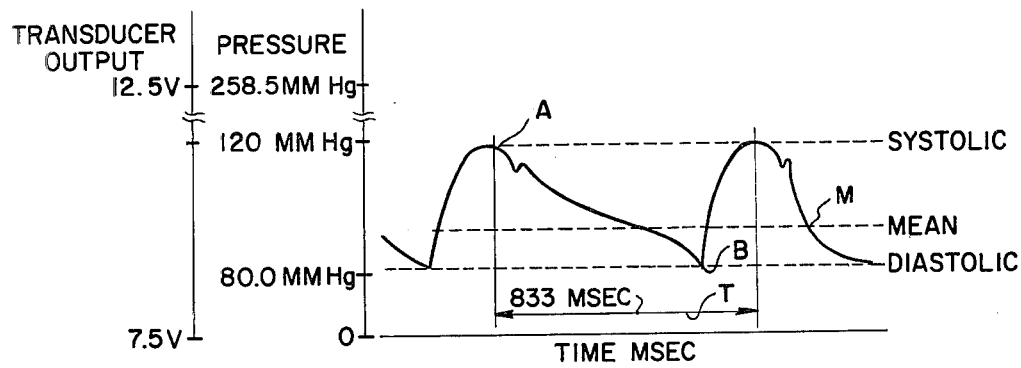
FIG. 1 is a graph showing the approximate variations of normal blood pressure.

With regard to the drawings and in particular FIG. 1, there is shown a waveform corresponding approximately to the variations in normal blood pressure. Typical values of systolic blood pressure are approximately 110mm Hg to 150mm Hg and of diastolic blood pressure are approximately 70mm Hg to 93mm Hg. Under certain abnormal situations, the systolic blood pressure may vary from 80mm Hg to 200mm Hg and the diastolic blood pressure may vary from 55mm Hg to 110mm Hg. In view of these considerations, the total range of pressure measurement desired is from 55mm Hg to 200mm Hg. Incorporating an added margin for safety, the total pressure range of interest is considered to lie from 0mm Hg to approximately 250mm Hg.

In FIG. 2, there is shown in block diagram form a blood pressure monitoring system in accordance with the teachings of this invention capable of measuring and displaying the systolic, diastolic and mean blood pressure over a range of 0 to approximately 250mm Hg. In particular, such a system includes a pressure transducer 10 capable of providing an output that varies linearly with pressure. The pressure transducer 10 as generally shown in FIG. 2 is more fully illustrated in FIG. 6 as comprising a pressure transducer 96 of the type manufactured by National Semiconductor Incorporated under type designation LX1601 G or D. In use, the transducer 96 is coupled to measure the blood pressure of a patient through a tube 82 having one end to which is connected a needle or catheter 80 to be inserted into a blood vessel of the patient. A saline solution may be introduced through port 88 to provide a fluid pathway from the patient's blood to the transducer 96. The other end of the tube 82 is coupled to a housing 84 through an input port 86. The blood pressure is coupled to a membrane 90 by the saline pathway and from a second membrane 92 through a noncompressible, nonconductive fluid medium 94, such as silicone oil, contained within a housing 95, to the transducer 96. In particular, the pressure exerted against the membrane 90 is transferred through the second membrane 92 to the fluid medium 94, which in turn exerts a pressure upon the transducer 96 to provide an output indicative thereof. An annular-shaped flange 89 extends downwardly from the housing 84 and has a series of threads disposed upon the interior periphery thereof. In a cooperating fashion, the housing 95 has a set of threads on the exterior periphery thereof whereby the housing 84 may be screwed onto the housing 95. As a result, after the blood pressure of one patient has been measured, the housing 84 may be simply removed and disposed of, and a new housing threadably coupled with respect to the transducer 96. Further, the second membrane 92 is supported by an annular member 91 secured to the interior periphery of the housing 95, whereby the membrane 92 is disposed into intimate contact with the membrane 90, when the housing 84 has been secured to the housing 95. As mentioned above, the output of the transducer 96 linearly varies with changes in pressure from 0mm Hg to approximately 250mm Hg; the National Semiconductor transducer referred to above is capable of providing a linear output within 1.5 percent over the total range with a sensitivity of 19.34 mV/mmHg. As indicated in FIG. 1, the output of the noted transducer 96 varies from 7.5V to 12.5V for such a variation in blood pressure.

The output of the pressure transducer 10 is applied to a filter 12 to remove certain undesired high-frequency components therefrom. In determining the desired frequency content of a signal being monitored, there are two assumptions made: (1) The fundamental frequency is a significant component; and (2) the upper frequency limit is placed at the Nth harmonic of the maximum heart beat rate of interest. The Nth harmonic is chosen as a compromise between noise rejection and the attenuation of the signal to be measured. The worst condition contemplated occurs during ventricular tachycardia, when a maximum heart rate of approximately 250 beats per minute occurs. Varying the selected harmonic of the fundamental frequency results in a corresponding variation of the filter set point and the amount of signal attenuation by the filter. For example, where the maximum heart rate is determined as 250 beats per minute, the fundamental frequency of the pressure waveform is 4.17Hz. By setting the upper frequency limit at the seventh harmonic, approximately 95% of the signal passes through the filter, and the resulting filter set point is set at 29.19Hz. If the filter set point is set at the tenth harmonic of the fundamental frequency, approximately 96% of the power is obtained and the filter set point of the filter 12 is 41.7Hz.

In a further embodiment of this invention, it is desired to permit adjustment of the maximum frequency passed by the filter 12. As will be explained in greater detail with respect to FIG. 4A, the filter 12 includes resistors R1 and R2 which may be of the variable resistance type, whereby the frequency set point of the filter 12 may be adjusted. Thus, an operator would be able to set the filter point of filter 12 dependent upon the intrinsic rate of the patient. For example, if the intrinsic heart rate of the patient is 60 beats per minute (1Hz), the set point of the filter at the seventh harmonic is 7Hz. Likewise, for an intrinsic rate of 120 per minute (2Hz), the filter set point is set at 14Hz for the seventh harmonic of the fundamental frequency. Further, the output of the transducer 10 may contain high-frequency artifact components due to inadvertent catheter movement. By variably setting the maximum frequency of the filter 12, the signal-to-noise ratio may be reduced, whereby the high-frequency components of such catheter movement may be minimized.

The output of the filter 12 is applied to each of a maximum peak detector 14, a minimum peak detector 16 and a mean detector 18, the outputs of which respectively provide indications of the systolic blood pressure, the diastolic blood pressure and the mean blood pressure of the patient. As will be explained in detail later, the mean detector 18 takes the form of an integrator for providing a signal indicative of the average blood pressure of the patient in accordance with the equation (1), set out above. One of the outputs of the detectors 14, 16 and 18 is applied by a switch 20 selectively set to one of three positions a, b and c corresponding to the outputs of the maximum peak detector 14, the minimum peak detector 16 and the mean detector 18, respectively, to a voltage-controlled oscillator 22, the output of which varies at a frequency proportional to the amplitude of the selected input signal. Thus, in one illustrative embodiment of this invention, the output of the voltage-controlled oscillator 22 is adjusted to vary from 0 to 1,000 Hz for a corresponding output of the pressure transducer 10 varying from 7.5 to 12.5V. Thus, an output of the voltage-controlled oscillator 22 of 1,000 Hz indicates a blood pressure of 258.5mm Hg and an output of 0Hz indicates a measured blood pressure of 0mm Hg.

The output of the voltage-controlled oscillator 22 is selectively gated through a gate 24 to be received and counted by a counter 28; the count so derived is indicative of the blood pressure and is suitably displayed as upon a digital display 30. A clock circuit 26 generates a gating clock signal in the form of a series of gating pulses as shown in FIG. 3B, each having a pulse width of substantially fixed duration and selected to permit a plurality of cycles of the oscillator output corresponding to the maximum blood pressure of interest, i.e., 258.5mm Hg pass through the gate 24 and to be counted by the counter 28. Thus, for a maximum pressure of 258.5mm Hg corresponding to a signal output of 1,000 Hz signal, a gating pulse width of 258.5 msec is required.

Further, the clock circuit 26 generates a train of latch pulses as shown in FIG. 3C, to be applied to the counter 28, whereby the counter 28 transfers a signal indicative of the counted oscillator pulses to the digital display 30. In addition, the clock circuit 26 generates a clear signal having a square waveform and a period of 1.5 seconds, to be applied to the counter 28, whereby the counted information is cleared so that the next series of pulses may be entered and counted by the counter 28. The period of the clear and latch signals is selected in accordance with that period of time in which a set of digits as displayed upon the digital display 30 may be recognized by a viewer and also in accordance with the minimum blood pressure to be monitored by the system. In this regard, it is noted that a heart pulse beat rate of 72 per minute is considered normal, but that well-conditioned athletes may have a heart rate as low as 50 beats per minute or 1 beat every 1.2 seconds. To accommodate a heart beat rate of 50 beats per minute, a sampling period and therefore a display period in excess of 1.2 seconds is required; in one illustrative embodiment of this invention, a sampling-display period of 1.5 seconds is provided as indicated in FIG. 3A. The gating pulse goes low after the clearing of the counter 28, whereby the counting of the train of pulses generated by the voltage-controlled oscillator 22 is initiated. After a period illustratively set at 258.5msec. in which pulses are counted by the counter 28, a latch pulse is generated thereafter to permit transfer of the pulse count to the digital display 30 for display thereby. The voltage controlled oscillator 22, the gate 24, the clock circuit 26, and the counter 28 serve as a processing circuit for providing a signal to the display 30 indicative of the patient's blood pressure.

In a further embodiment of this invention as illustrated in FIG. 2, the output of the maximum peak detector 14 is applied to a threshold amplifier 19 which provides an output indicative of a maximum value of blood pressure above preselected critical limits, to actuate an alarm 21. In a similar fashion, the output of the minimum peak detector 16 is applied to a threshold amplifier 23, which provides an output indicative that a blood pressure value has been detected that is less than a preselected, acceptable limit. In turn, the output of the threshold amplifier 23 energizes an alarm 25, whereby attention may be given to the patient whose blood pressure is being monitored. In a further aspect of this invention, a differentiating circuit 17 may also be associated with the maximum peak detector 14, whereby the rate of change of the systolic blood pressure signal may be measured and if in excess of a given rate as detected by the threshold amplifier 19, the alarm 21 is energized. In a similar fashion, the output of the minimum peak detector 16 may be associated with a differentiating circuit 27 for detecting the rate of change of the diastolic blood pressure. If the rate of change of the systolic blood pressure exceeds a given level as detected by the threshold amplifier 23, the alarm 25 is actuated. In this manner, the systolic and diastolic blood pressures, as well as their rates of change, may be monitored and if preselected maximum and minimum values of blood pressure or rates of change thereof are exceeded, alarms are actuated to bring assistance to the patient.

Figure 4D:
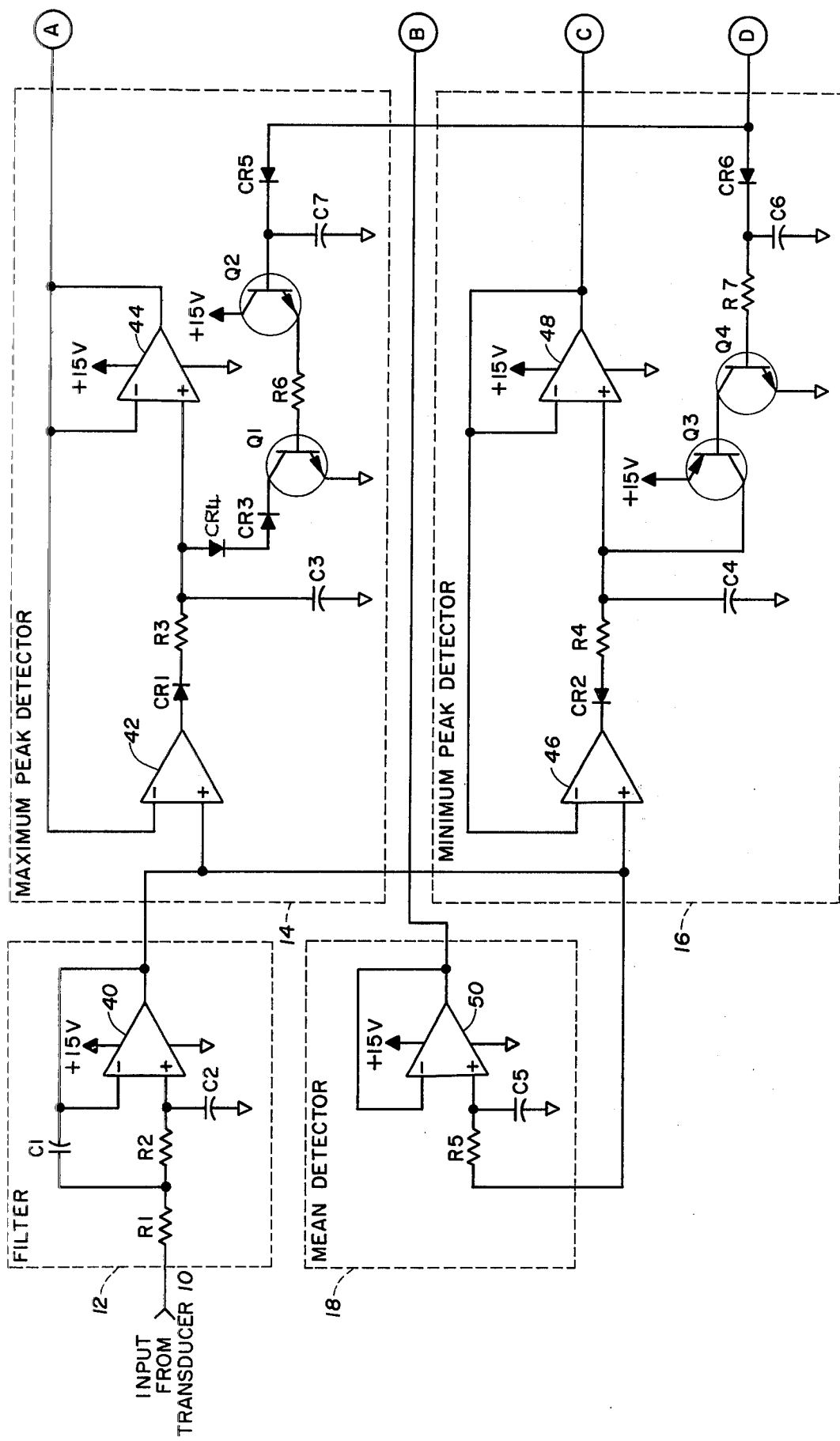
FIGS. 4A and 4B are a detailed circuit diagram of one illustrative embodiment of the blood pressure monitoring system as generally shown in FIG. 2.
Figure 4B:
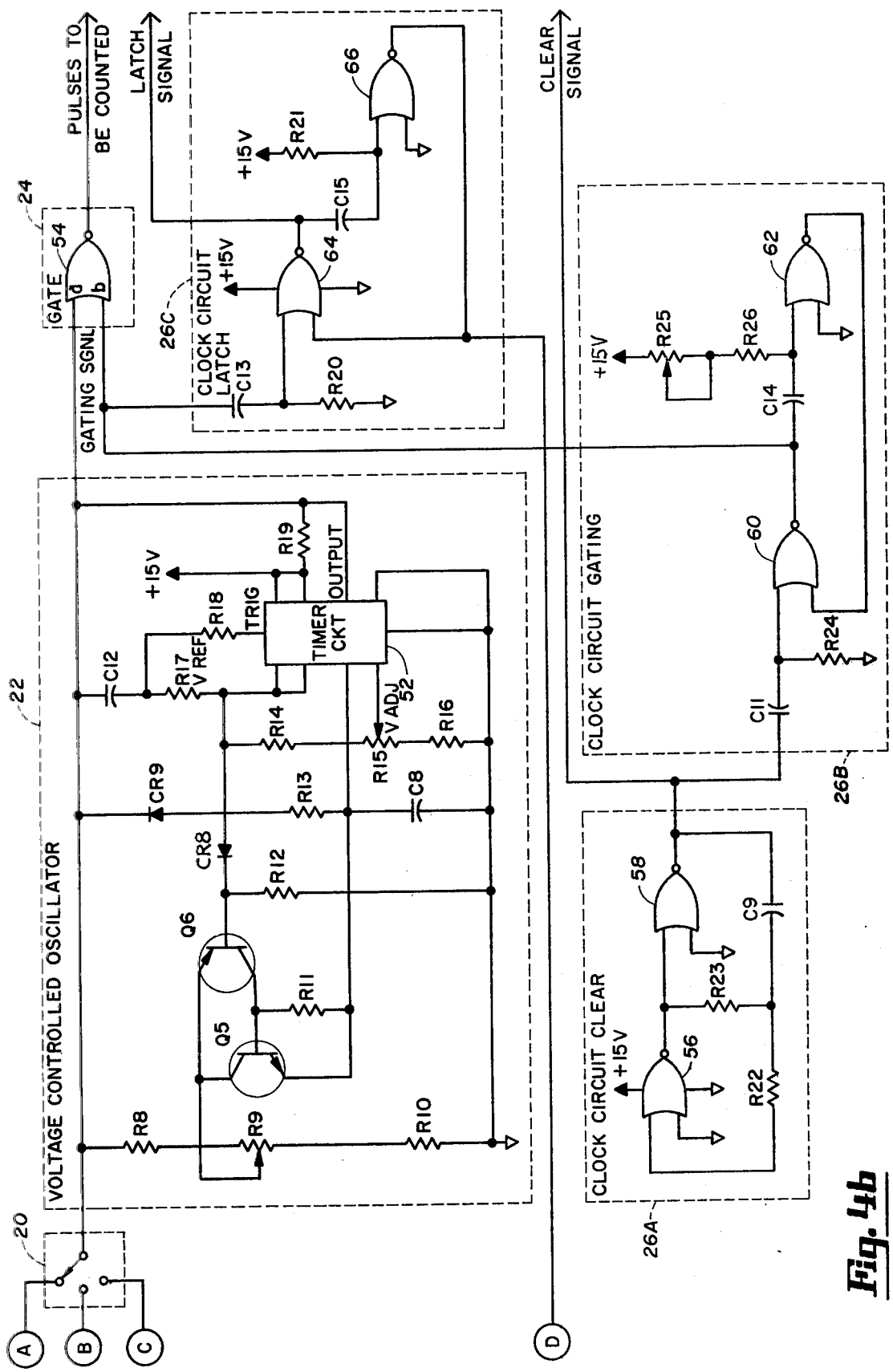

In FIG. 4, there is shown a detailed schematic drawing of an illustrative embodiment of the blood pressure monitoring system as shown diagrammatically in FIG. 2; the diagrammatic blocks shown in FIG. 2 also are shown in FIG. 4 and are similarly labeled and numbered. The output of the pressure transducer 10, not shown in FIG. 4, is applied to the filter 12 through resistances R1 and R2 to the plus input of an operational amplifier 40. As mentioned above, the set point for the filter 12 illustratively set in the range of 20 to 42 Hz, whereby those frequency components above the highest pulse beat of interest, are substantially attenuated. As set out below, the values of the capacitors C1 and C2 and the resistors R1 and R2 are set to provide the desired filter cutoff point.

The output derived from the filter 12 is applied to each of the maximum peak detector 14, the minimum peak detector 16, and the mean detector 18. The circuit construction of the detectors 14 and 16 are quite similar. In particular, the maximum peak detector 14 comprises an operational amplifier 42 upon which the filtered output is applied, and in turn, whose output is applied through a diode CR1 and resistor R3 to the plus input of an operational amplifier 44. The output of the operational amplifier 44 is in turn applied to the switch 20 and also fed back to the minus terminal of the operational amplifier 42. In operation, the filtered output is applied through the operational amplifier 42 to charge the capacitor C3 is accordance with the filtered output. The capacitor C3 charges to that maximum value of the blood pressure signal occurring within a sampling period determined by the clock circuit 26 in a manner to be explained in detail later. Generally, the maximum peak detector 14 is reset in response to the last signal generated by the clock circuit 26 and applied through a diode CR5 to actuate transistor Q2, which in turn renders conductive transistor Q1 to discharge the capacitor C3 to ground through diodes CR3 and CR4. Thus, the capacitor C3 charges to a maximum value corresponding to the systolic pressure and at that point, discharge of the voltage stored on the capacitor C3 is prevented by the diode CR1. The maximum value as stored upon the capacitor C3 for that sampling period is applied through the operational amplifier 44 to the switch 20. Significantly, the operation of the maximum peak detector 14, and in particular the capacitor C3 and the diode CR1, serve not only to measure the peak or systolic value of blood pressure, but also to store the peak value for the remaining portion of the sampling period until the maximum peak detector 14 is reset.

As explained above, the sampling period is set according to that time period in which an indication of the blood pressure is displayed and also to permit at least one cycle of the blood pressure signal at the lowest pulse rate of interest, e.g. 50 pulses/minute, to be read within a sampling period. Illustratively, the sampling period is set at 1.5 seconds.

A further concern in the design of the maximum peak detector 14 is the amount of output drift due to the input bias of the operational amplifier 42 and the leakage occurring in the capacitor C3 and the diode CR1. As set forth below, operational amplifiers are available and values of CR1 and C3 chosen to provide a leakage that is acceptable so that an accurate maximum systolic value blood pressure is provided, for the sampling rates of interest.

The filtered output also is applied to the minimum peak detector 16 and in particular to the plus terminal of an operational amplifier 46, the output of which is applied through a diode CR2 and a resistor R4, to charge capacitor C4 to a voltage indicative of the minimum or diastolic value of the blood pressure during a sampling period. In turn, the value of the capacitor C4 so charged, is applied to the plus terminal of the operational amplifier 48, the output of which is applied to the switch 20 and also to the minus terminal of the operational amplifier 46. In a manner similar to that of the maximum peak detector 14, the minimum peak detector 16 is reset by a signal developed by the clock to render transistor Q4 conductive, whereby capacitor C4 is charged through transistor Q3 toward the supply voltage. The circuit difference between the minimum and maximum peak detectors 14 and 16 resides in the manner in which their diodes CR1 and CR2 are biased with respect to preventing the discharge of their corresponding capacitors C3 and C4. In the minimum peak detector 16, the diode CR2 is arranged so as to prevent the further charging of the capacitor C4 once a minimum value is stored thereon. Further, in resetting the minimum peak detector 16, the capacitor C4 is charged to a maximum value, from which it is discharged as the input signal applied through the operational amplifier 46 goes toward a minimum value during a sampling period.

In addition, the filtered output derived from the filter 12 is applied to a mean detector 18, which essentially comprises an integrating circuit made up of a resistor R5, a capacitor C5 and an operational amplifier 50. The output of the operational amplifier 50 provides an average value in accordance with equation (1), given above. The circuit of the mean detector 18 operates as an integrator if the frequency content of the signal is significantly greater than $1/R5 \times C5$; as set out below, the values of R5 and C5 are selected to insure that this condition is met.

The outputs of each of the detectors 14, 16 and 18 are respectively applied to the three terminals $a$, $b$ and $c$ of the switch 20. In operation, the operator selects the desired position of the switch 20 to provide upon the display 30 either the systolic, diastolic or mean value of blood pressure.

The selected output as derived from the switch 20 is applied to the voltage-controlled oscillator 22, the output of which is applied to the gate 24 and whose frequency varies as a function of the magnitude or level of its input signal. The input signal derived from switch 20 is applied through the resistor R8 to a pair of transistors Q5 and Q6, which act together as a constant current source to charge the capacitor C8. When the level of the voltage charged by capacitor C8 exceeds a reference level as determined by the biasing voltage developed upon resistor R15 and applied to the Vadj. terminal of a logic circuit or timer 52, the output goes to zero. At this point, the capacitor C12 begins to charge through resistance R17, thereby varying the voltage applied to the trigger terminal of the timer 52. When the trigger level exceeds the reference voltage as applied to the corresponding terminal of the timer 52, i.e., the voltage developed across resistors R14, R15 and R16, the output of the timer 52 goes high and remains high until the capacitor C8 charges to the voltage level Vadj. In this manner, the voltage-controlled oscillator 22 varies from low to high, and high to low, in accordance with the level of the input derived from switch 20. As the voltage level of the input increases, the faster capacitor C8 charges and as a result, the higher the frequency of the output as derived from the timer 52.

The output of the voltage oscillator is set to vary from 0 to 1,000 Hz for a range of blood pressure from 0 to 258.5mm Hg, and is applied to terminal $a$ of the gate 24, illustratively taking the form of a C-MOS NOR gate 54. The NOR gate 54 is enabled or gated by a gating signal developed by a gating clock circuit 26b in a manner to be described later. Further, the output of the NOR gate 54 is applied to a counter and display circuit as more specifically described with respect to FIG. 5, hereinafter.

As described above, a latch or clock signal is provided by the clear clock circuit 26a in the form of a train of pulses whose period is in the order of 1.5 seconds. The period is set in order to permit at least one cycle of the blood pressure signal of the lowest pulse rate of interest, to be sampled, as well as to provide a display for a period that is easily recognizable. With respect to FIG. 4, the clear clock circuit 26a comprises a first, C-MOS NOR gate 56, the output of which is coupled to one of the inputs of a second similar NOR gate 58. The output of the NOR gate 58 is in turn connected through a capacitor C9 and the resistor R22 to an input of the NOR gate 56. The point of interconnection between the resistor R22 and the capacitor C9 is coupled by a resistor R23 to each of the output of NOR gate 56 and the input of NOR gate 58. The clear clock circuit 26a is astable, i.e., free-running, at a frequency to achieve the desired sampling period. In operation, if a 1 signal is presented to the input of the NOR gate 58, its output is zero, thereby causing capacitor C9 to charge through resistor R23 to which is applied a 1 or high signal. Once capacitor C9 has charged to the threshold level of NOR gate 56, i.e., a high or 1 signal applied thereto, the output of NOR gate 56 goes low or 0, thereby causing a discharge at capacitor C9 through resistor R23 until a zero is placed upon the NOR gate 56, at which time it changes its output state to 1. Thus, the astable, clear clock circuit 26a provides a free-running signal of a defined period determined by the values of capacitor C9 and resistor R23, as will be set out specifically below. The output of the clear clock circuit 26a provides the clear signal which is used to reset the counter 28 and also to initiate the timing operations of the gating clock circuit 26b and the latch clock circuit 26c in a manner to be explained.

The gating clock circuit 26 receives the free-running clock signal as generated by the clear clock circuit 26a and shown in FIG. 3A; in particular, the free-running clock output is coupled through capacitor C11 to a C-MOS NOR gate 60, the output of which is applied through a capacitor C14 to one of the terminals of a C-MOS NOR gate 62. The output of the NOR gate 62 in turn is applied to another input of the NOR gate 60. The capacitor C14 is charged through resistors R25 and R26. In operation, the pulse output of the clear clock circuit 26a is applied to the gating clock circuit 26b to apply a high or 1 signal to one of the inputs of the NOR gate 60, whereby its output is driven low. At this time, the capacitor C14 is charged through the resistors R25 and R26 until the threshold level of the NOR gate 62 is reached, at which time its output is driven to 0 and as a result, the output of the NOR gate 60 is driven high. Therefore, an output is derived from the NOR gate 60 and is used as a gating pulse signal as shown in FIG. 3B to gate selectively the output of the voltage-controlled oscillator 22 through the gate 24 to be counted by the counter 28. As mentioned above, the pulse width of the gating pulse is set to permit a number of pulses as generated by the oscillator 22 to pass therethrough corresponding to the maximum blood pressure of interest. Illustratively, the substantially fixed period is set an an illustrative value of 258.5 msec. as determined by the values of the resistances R25 and R26 and of capacitor C14, given particularly below.

Further, the output of the clock gating circuit 26b is applied to the latch clock circuit 26c to initiate its timing operation. The latch clock circuit 26c takes the form of a monostable circuit comprising a NOR gate 64 having one terminal to which the gating signal is applied and whose output is applied through a capacitor C15 to one terminal of a NOR gate 66. The output of the NOR gate 66 is connected to the other terminal of the NOR gate 64 and provides one output of the latch clock circuit 26c to be applied to reset the maximum and minimum peak detector circuits 14 and 16. The capacitor C15 is charged by a positive voltage source through a resistor R21. The structure and operation latch clock circuit 26c is similar to that of the gating clock circuit 26b and the pulse width of its output signals is determined by the values of the resistor R21 and the capacitor C15, values of which are illustratively given below. In one illustrative embodiment of this invention, the values of the resistor R21 and the capacitor C15 are set to provide an output clocking pulse of a width of 100 $\mu$sec. A further output of the circuit 26c is taken from the output of the NOR gate 64 to provide a latch pulse signal to transfer data from counter 28 to the digital display 30, as shown in FIG. 2.

In FIGS. 3A, 3B and 3C, the timing relationships between the output of the clock circuits 26a, 26b and 26c are shown. In summary, the output of the clear clock circuit 26a is used to initiate the timing operation of the gating clock circuit 26b to generate a gating pulse signal of a pulse width of 258.5 msec. In turn, the output of the clock gating circuit 26b is used to initiate the operation of the latch clock circuit 26c to generate a latch pulse signal of a pulse width of 100 $\mu$sec. In overall system operation, the digital display 30 is set at the same time that the pulses to be counted are gated through the gate 24. After the information has been gated and counted by the counter 28, the information is transferred to the digital display 30 in response to the latch signal. It is noted that the period of repetition of the gating pulse signals and the latch pulse signals is set in accordance with the astable, clear clock circuit 26a and in one illustrative embodiment of this invention is in the order of 1.5 seconds. As explained above, one of the outputs of the latch clock circuit 26c is used to reset the minimum and maximum peak detectors 14 and 16. Thus, the free-running clear clock circuit 26a is used to control the period at which the blood pressure signal is sampled, and to control the gating of the voltage-controlled oscillator 22 to the counter, and to latch information from the counter to the digital display, without need for expensive peak detecting apparatus or for synchronizing the gating clocks to the detection of the minimum and maximum peaks of the blood pressure signal. As a result, the blood pressure monitoring system of this invention is greatly simplified and its cost significantly reduced.

With respect to FIG. 4, particular, illustrative values of the various components shown therein, as well as the designations of the logic circuits incorporated into the circuit of FIG. 4, are set forth below:

| ELEMENTS | VALUE OR TYPE |
|---|---|
| R1 | 1M |
| R2 | 1M |
| R3 | 1K |
| R4 | 1K |
| R5 | 1M |
| R6 | 3K |
| R7 | 750K |
| R8 | 20K |
| R9 | 2K |
| R10 | 15K |
| R11 | 1M |
| R12 | 200K |
| R13 | 2K |
| R14 | 1K |
| R15 | 1K |
| R16 | SEL(8K) |
| R17 | 4.7K |
| R18 | 100 |
| R19 | 1K |
| R20 | 10K |
| R21 | 100K |
| R22 | 2M |
| R23 | SEL(680K) |
| R24 | 10K |
| R25 | SEL(100K) |
| R26 | 300K |
| C1 | .022 $\mu$f |
| C2 | .01 $\mu$f |
| C3 | 1 $\mu$f POLYCARB |
| C4 | 1 $\mu$f POLYCARB |
| C5 | 1 $\mu$f POLYCARB |
| C6 | 1000 pf |
| C7 | 330 pf |
| C8 | .1 $\mu$f POLYCARB |
| C9 | 1 $\mu$f TANT |
| C11 | 1000 pf |
| C12 | 4700 pf |
| C13 | 1000 pf |
| C14 | 1 $\mu$f TANT |
| C15 | 1000 pf |
| Q1 | 2N4401 |
| Q2 | 2N4401 |
| Q3 | 2N4403 |
| Q4 | 2N4401 |
| Q5 | 2N2484 |
| Q6 | 2N2907 |
| CR1 | FD2473 |
| CR2 | FD2473 |
| CR3 | FD2473 |
| CR4 | FD2473 |
| CR5 | FD2473 |
| CR6 | FD2473 |
| CR7 | FD2473 |
| CR8 | FD2473 |
| CR9 | FD2473 |
| 40 | LM 324 |
| 42 | LM 324 |
| 44 | LM 312 |
| 46 | LM 324 |
| 48 | LM 312 |
| 50 | LM 312 |
| 52 | LM 322 |
| 54 | CD 4001A |
| 56 | CD 4001A |
| 58 | CD 4001A |
| 60 | CD 4001A |
| 62 | CD 4001A |
| 64 | CD 4001A |
| 66 | CD 4001A |

The logic elements illustratively designated above are designated in accordance with those types as manufactured by the National Semiconductor Corporation and RCA.

Figure 5:
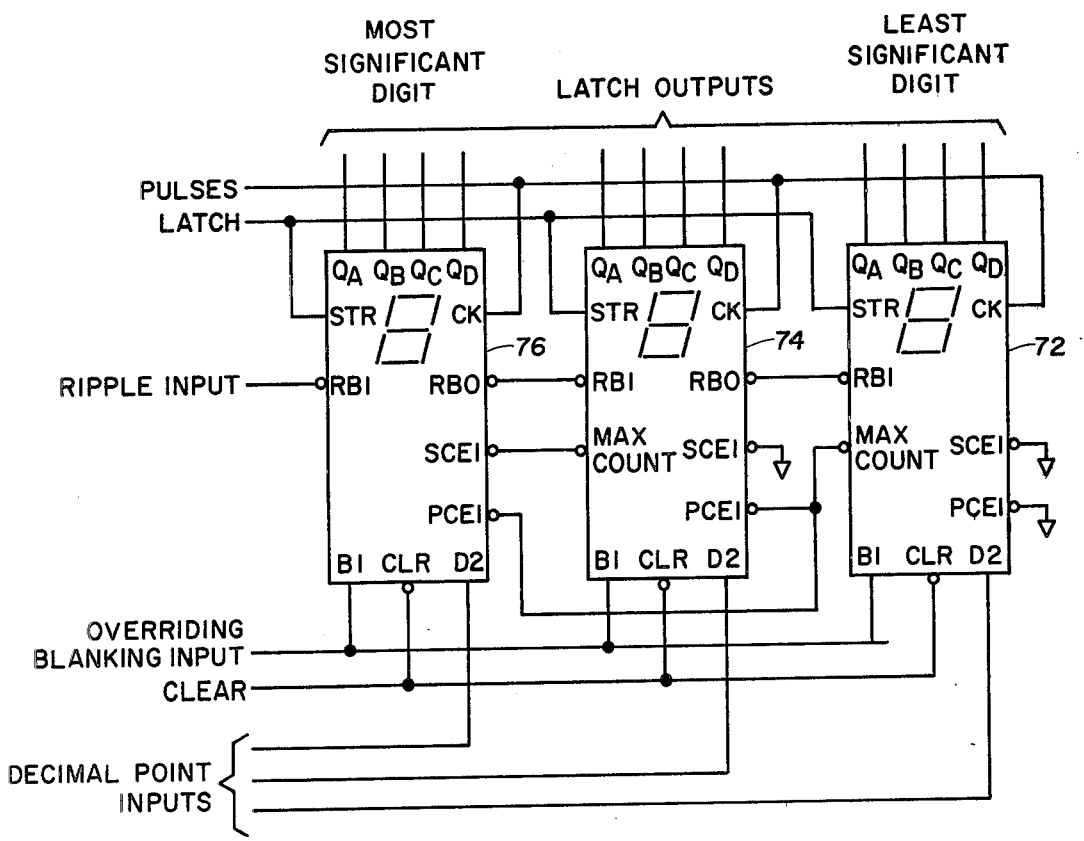
FIG. 5 is a circuit diagram of the counter and display circuit for receiving the outputs of the blood pressure monitoring system as shown in FIG. 4.

The latch pulse signal, the clear pulse signal and the pulses as generated by the voltage-controlled oscillator 22 to be counted are applied in one illustrative embodiment to a counter and display circuit as shown in FIG. 5. The circuit of FIG. 5 differs from that illustrated in FIG. 2 in that the counting and display operations for a single digit are combined into a single logic circuit of the type TIL306 as manufactured by Texas Instruments. In particular, the pulses to be counted are applied to the clock terminal of each of the logic circuits 72, 74 and 76. In FIG. 5, there is shown three logic circuits 72, 74 and 76 capable of providing a digital display of three digits. In operation, the one's digit counter 72 counts digits 1 to 9, after which the ten's digit counter 74 is pulsed once. In turn, when the ten's digit counter 74 has counted to 9, upon receipt of the next pulse, the ten's digit counter 74 is reset to 0 and a 1 pulse is applied to the 100's digit counter 76. Upon receipt of the latch signal, the logic circuits 72, 74 and 76 display the indicated count upon their displays for a period terminating upon receipt of the next latch signal.

Numerous changes may be made in the abovedescribed apparatus and the different embodiments of the invention may be made without departing from the spirit thereof; therefore, it is intended that all matter contained in the foregoing description and in the accompanying drawings shall be interpreted as illustrative and not in a limiting sense.

What is claimed is:

1. A system for monitoring the blood pressure of a patient, said system comprising:
   a. transducer means adapted to be coupled to the vascular system of the patient for providing an output indicative of the patient's blood pressure;
   b. filter means having a variable limit set in accordance with the patient's heartbeat for removing a high portion of the undesired frequency components from the output of said transducer means, the set limit being high with respect to the patient's heart rate, said filter means passing a high portion of the signal components of a frequency corresponding to the patient's heart rate;
   c. systolic detector means responsive to the output of said transducer means for providing a first output indicative of the maximum magnitude of the patient's blood pressure;
   d. diastolic detector means responsive to the output of said transducer means for providing a second output indicative of the minimum magnitude of the patient's blood pressure;
   e. display means for displaying an indication of the patient's blood pressure;
   f. switch means for selecting one of the first and second outputs to be displayed; and
   g. processing means responsive to the magnitude of the selected output for providing an output indicative thereof for a selected period to said display means.

2. The system as claimed in claim 1, wherein there is further included mean detector means responsive to the output of said transducer means to provide a third output indicative of the mean blood pressure of the patient, and said switch means including means disposable to one of three positions to selectively apply one of the first, second and third outputs to said processing means.

3. The system as claimed in claim 1, wherein said filter means filters signal components of a frequency corresponding to the Nth harmonic of the variable pulse beat rate of the patient to be monitored by said system, said Nth harmonic being set in the range of the seventh to tenth harmonic of the patient's heart rate.

4. A system for monitoring the blood pressure of the patient, said system comprising:
   a. transducer means adapted to be directly coupled to the vascular system of the patient for providing an output indicative of the patient's blood pressure;
   b. filter means having a variable limit set in accordance with the patient's heart beat for removing a high proportion of the undesired frequency component from the output of said transducer means, the set limit of said filter means being high with respect to the patient's heart rate, said filter means passing a high portion of the signal components of a frequency corresponding to the patient's heart rate;
   c. systolic detector means responsive to the output of said transducer means for providing a first output indicative of the maximum magnitude of the patient's blood pressure;
   d. diastolic detector means responsive to the output of said transducer means for providing a second output indicative of the minimum magnitude of the patient's blood pressure;
   e. display means for displaying an indication of the patient's blood pressure;
   f. switch means for selecting one of the first and second outputs to be displayed by said displaying means; and
   g. processing means responsive to the magnitude of the selected output as derived from said switch means, for providing an output indicative thereof for a selected period of time to said display means.

5. The system as claimed in claim 4, wherein said transducer is of the catheter type.

* * * * *